United States Patent [19]

Curran

[11] 4,051,139

[45] Sept. 27, 1977

[54] PYRIDINE GRIGNARD DERIVATIVES

[75] Inventor: Adrian Charles Ward Curran, Newcastle-upon-Tyne, England

[73] Assignee: John Wyeth & Brother Limited, Maidenhead, England

[21] Appl. No.: 638,384

[22] Filed: Dec. 8, 1975

Related U.S. Application Data

[62] Division of Ser. No. 526,353, Nov. 22, 1974, Pat. No. 3,963,722.

[30] Foreign Application Priority Data

Nov. 26, 1973 United Kingdom ............... 54728/73
Mar. 27, 1974 United Kingdom ............... 13516/74

[51] Int. Cl.$^2$ .................. C07D 221/16; C07D 215/14; C07D 215/06; C07D 215/12
[52] U.S. Cl. .......................... 260/290 HL; 260/283 R; 260/297 B; 260/297 T
[58] Field of Search .................. 260/290 HL, 283 CF, 260/283 R

[56] References Cited

U.S. PATENT DOCUMENTS

| | | | |
|---|---|---|---|
| 2,838,508 | 6/1958 | Ramsden | 260/290 HL |
| 3,083,242 | 3/1963 | Ramsden | 260/290 HL |
| 3,096,370 | 7/1963 | Bloom et al. | 260/290 HL |

OTHER PUBLICATIONS

Paradise, et al., Chemical Abstracts, vol. 70, (1969) p. 358, abst. 115,199j.
Esafov et al. ibid, vol. 74, (1971) p. 430 abst. 76,276t.

*Primary Examiner*—Donald G. Daus
*Assistant Examiner*—David E. Wheeler
*Attorney, Agent, or Firm*—Arthur E. Wilfond

[57] ABSTRACT

The invention relates to magnesium halide derivatives of tetrahydroquinolines and related compounds. These are intermediates useful in the preparation of anti-ulcer agents.

10 Claims, No Drawings

PYRIDINE GRIGNARD DERIVATIVES

This is a division of application Ser. No. 526,353, filed Nov. 22, 1974 and now U.S. Pat. No. 3,963,722.

The invention relates to processes for preparing pyridine derivatives and to novel intermediates used therein.

In copending U.S. Ser. No. 460,265 filed April 11, 1974 (and now abandoned) entitled "Pyridine Derivatives": inventors Adrian C. W. Curran, Roger Crossley and David G. Hill there are described novel compounds of formula I

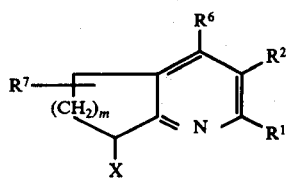

and acid addition salts thereof, wherein $R^1$, $R^2$ and $R^6$ are the same or different and represent a hydrogen atom, a trifluoromethyl group, or an alkyl, aralkyl or aryl radical, any of which radicals may be substituted by alkyl, alkoxy, halogen, nitro or trifluoromethyl or $R^1$ and $R^2$ taken together represent an alkylene chain —$CH_2(CH_2)_nCH_2$— wherein $n$ is 1, 2 or 3, $R^7$ represents single or multiple substitution by a hydrogen atom, or alkyl, aralkyl or aryl radicals any of which radicals may be substituted by alkyl, alkoxy, halogen, nitro or trifluoromethyl and when $R^1$ and $R^2$ taken together form an alkylene chain the resulting ring may be substituted by one or more $R^7$ radicals as defined above, X is cyano, $CONHR^3$, $CSNHR^3$ or $CO_2R^5$ wherein $R^3$ is selected from hydrogen or alkyl, or aralkyl radicals and $R^5$ is selected from a hydrogen atom or a lower alkyl, lower aralkyl or aryl radical any of which radicals may be substituted by alkyl, alkoxy, halogen, nitro or trifluoromethyl, and $m$ is 1, 2 or 3 and metal, e.g. alkali-metal, salts of the compounds in which $R^5$ is hydrogen.

Compounds of formula I wherein X is $CSNHR^3$ and some compounds, wherein X is CN, are anti-ulcer agents.

Compounds of formula I wherein X is $CO_2R^5$ and $R^5$ is as defined above are intermediates for corresponding compounds wherein X is $CONHR^3$. I have now found an alternative way of preparing compounds of formula I wherein X is $CO_2R^5$ involving novel intermediates.

According to the present invention there is provided compounds of formula (II)

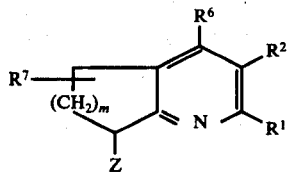

wherein $R^1$, $R^2$, $R^6$, $R^7$ and $m$ are as defined in connection with formula I and $m$ and $n$ may be the same or different, Z is MgHal or $CO_2$MgHal and Hal is chlorine, bromine or iodine.

Whenever the term "alkyl" radical is used in this specification it is preferred that this is a lower alkyl radical which may be a straight or branched chain, having from 1 to 6 carbon atoms, e.g. methyl, ethyl, n-, and iso-propyl and n-, s- and t-butyl, $R^7$ may be a gem-dimethyl group and when a single radical may be on the same carbon atom as the group Z. The term alkyl radical is also intended to embrace cyclic alkyl radicals e.g. cyclobutyl, cyclopentyl and cyclohexyl. When any of $R^1$, $R^2$, $R^6$ or $R^7$ is an aralkyl radical it is preferred that this is an aryl-lower alkyl radical where the lower alkyl portion may be as discussed above for a lower alkyl radical. The aryl portion is preferably a phenyl radical.

The term "alkoxy" means an alkyloxy group and the alkyl portion may have any of the meanings given above for the alkyl radical.

When any of $R^1$, $R^2$, $R^6$ or $R^7$ is an aryl radical, this is preferably phenyl or a substituted phenyl radical (substituted by alkyl, alkoxy, halogen, nitro or trifluoromethyl). However, other aryl radicals which may be used include naphthyl.

Particularly preferred compounds are those in which one of $R^1$, $R^2$ and $R^6$ is methyl and the other is hydrogen. Also preferred are compounds wherein $m$ is 2.

When $R^1$ and $R^2$ are joined to form an alkylene chain the compounds may be represented by formula:

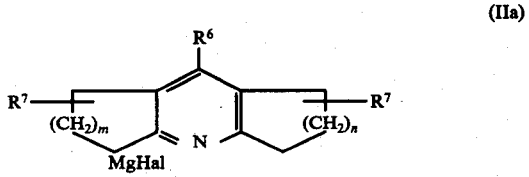

wherein $R^6$ and $R^7$ are as defined in connection with formula I, Hal is chlorine, bromine or iodine and $n$ and $m$ are each selected from 1, 2 and 3 and may be the same or different.

The compounds of formula II wherein Z is Mg Hal can be treated with carbon dioxide and then with a compound $R^5OH$, wherein $R^5$ is as defined in connection with formula I, to give corresponding compounds of formula I wherein X is $CO_2R^5$. This process is included within the present invention.

Treatment of a compound of formula (II) wherein Z is MgHal with carbon dioxide gives an intermediate of formula III, which can usually be isolated,

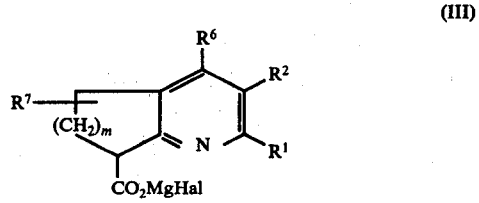

wherein $R^1$, $R^2$, $R^6$ and $R^7$ are as defined in connection with formula I and Hal is chlorine, bromine or iodine. Compounds of formula (III) and processes for preparing them are also included within the present invention as is the process of converting them to the corresponding compound of formula I wherein X is $CO_2R^5$ and $R^5$ is as defined in connection with formula I. The process may be carried out with a compound $R^5OH$ in the presence of an acid catalyst e.g. dry HCl gas or conc. sulphuric acid, or a Lewis acid catalyst e.g. boran trifluoride.

A compound of formula (IIa) with carbon dioxide gives an intermediate of formula (IIIa) which can usually be isolated

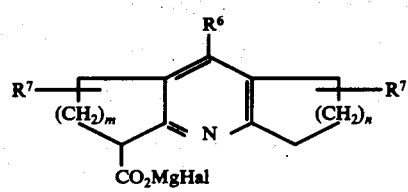

(IIIa)

wherein $R^6$, $R^7$, m and n are as defined in connection with formula IIa and Hal is chlorine, bromine or iodine.

The present invention also provides a process for preparing a compound of formula II wherein Z is MgHal which process comprises treating a compound of formula I wherein X is hydrogen with an alkyl magnesium halide $R^{11}$MgHal wherein $R^{11}$ is an alkyl group, preferably a lower alkyl group of 1 to 6 carbon atoms, and Hal is chlorine, bromine or iodine. $R^{11}$ may be a straight or branched chain alkyl group, the isopropyl group being presently preferred. The reaction is conducted in an inert atmosphere. It has been found preferable to conduct the above reaction with heat in the presence of an inert solvent with a boiling point in the range 100°-120°, e.g. toluene or dioxan, toluene being the preferred solvent. The reaction will take place in the absence of a solvent but we have found that the yields are then generally lower, unless an excess of the Grignard reagent e.g. 2:1 is used.

The present invention also provides a process for preparing a compound of formula IIa which process comprises treating a compound of formula IV

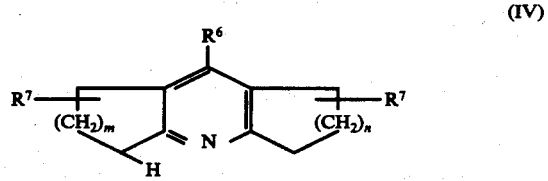

(IV)

wherein $R^6$, $R^7$, m and n are as defined in connection with formula IIa with an alkyl magnesium halide $R^{11}$MgHal wherein $R^{11}$ and Hal are as defined above. The reaction may be carried out as described above in connection with the preparation of compounds of formula II.

The following Examples illustrate the invention.

EXAMPLE 1

Methyl-3-methyl-5,6,7,8-tetrahydroquinoline-8-carboxylate

A stirred suspension of magnesium (139 g., 5.72 g. atom) in anhydrous ether (500 ml.), was treated under an atmosphere of dry nitrogen, with a solution of isopropylbromide (541 g., 4.4 mol) in anhydrous ether (400 ml.) at such a rate to maintain a gentle reflux. When the reaction was complete 3-methyl-5,6,7,8-tetrahydroquinoline (323 g., 2.2 mole) was added portionwise and the ether was removed by distillation. The residue was heated to an internal temperature of 120° for 1 hour during which time a vigorous evolution of gas was observed. The residue was diluted with dry toluene (270 ml.) and heating continued for a further 1 hour during which time a portion of the toluene (150 ml.) was allowed to distill. The residue was cooled, diluted with anhydrous ether (2 ml) and filtered in a nitrogen atmosphere to remove unreacted magnesium. The ethereal solution of 3-methyl-5,6,7,8-tetrahydroquinoline-8-magnesium bromide was added slowly, with vigorous stirring, to anhydrous ether (4 l.) whilst a rapid stream of $CO_2$ gas was bubbled through the mixture. The reaction was complete when the colour was discharged and a flocculent pale yellow solid precipitated. The solid (1.243 kg the magnesium bromide salts of 3-Methyl-5,6,7,8-tetrahydroquinoline-8-carboxylic acid and of isobutyric acid formed as a by product) was filtered, washed with anhydrous ether and dried and added portionwise with ice cooling to a vigorously stirred solution of methanol (3 l.) previously treated with dry hydrogen chloride. The reaction was stirred at room temperature for 8 hours and the volatile materials removed in vacuo. The residual oil was diluted with water (1 liter) and extracted with ether (3 × 500 ml.) and the extracts discarded. The aqueous solution was adjusted to pH 10.0 with sodium carbonate and extracted with ether (4 × 500 ml.). The combined extracts were washed with water (2 × 500 ml.) brine (2 × 500 ml.), dried ($MgSO_4$) and the solvent removed in vacuo to give the title compound as a pale yellow oil (366.5 g.) 72% pure by G.L.C.: 10% SE30, T = 200° C, $R_F$=3.25 min) b.p. 100°-110°/0.15 mm.

EXAMPLE 2

Methyl-3-methyl-5,6,7,8-tetrahydroquinoline-8-carboxylate

To a stirred suspension or magnesium turnings (12.48 g., 0.52 g. atom) in anhydrous ether (50 ml.) and in an atmosphere of nitrogen was added a solution of ethyl bromide (43.6 g. 0.4 mol.) in anhydrous ether (40 ml.) at such a rate as to maintain a gentle reflux. When the reaction was complete 3-methyl-5,6,7,8-tetrahydroquinoline (29.4 g. 0.2 mol.) was added portionwise with stirring. The reaction mixture was heated at 80° and the ether removed by distillation and the residue heated at 80° for a further 2 hours, cooled and diluted with anhydrous ether. The ethereal solution of 3-methyl-5,6,7,8-tetrahydroquinoline-8-magnesium bromide was treated with $CO_2$ gas until the red colour was discharged and the solid filtered off then washed with ether and dried. The resulting 3-methyl-5,6,7,8-tetrahydroquinoline-8-carboxylic acid magnesium bromide salt was added portionwise with stirring to an ice-cold solution of methanol saturated with HCl gas (500 ml.) and allowed to stand at room temperature for 15 hours. The solvent was removed in vacuo and the residue dissolved in water (100 ml.) and extracted with ether (3 × 50 ml.) and the extracts discarded. The aqueous solution was adjusted to pH 10.0 with sodium carbonate and extracted with ether (3 × 50 ml.). The combined ethereal extracts were washed with brine, dried and the solvent removed to give a pale yellow oil (25 g) which contained the title compound (7%) and unreacted 3-methyl-5,6,7,8-tetrahydroquinoline (93%) by G.L.C. analysis.

EXAMPLE 3

Methyl-1,2,3,4,5,7,8,9,10,11-decahydro-dicyclohepta-[b,e]pyridine-5-carboxylate and corresponding 5-carboxamide A mixture of cycloheptanone (190 g.) and 2-(dimethylaminomethyl)-cycloheptanone (72 g.) was heated at 170° C for 12 hours. The excess cycloheptanone was removed and the residue dissolved in ethanol (300 ml.), treated with hydroxylamine hydrochloride (100 g.) and the mixture heated at reflux for 2 hours, cooled, diluted with water (1 liter) and extracted with ether (2 × 300 ml.). The aqueous phase was adjusted to pH10 with sodium carbonate and extracted with ether (3 × 250 ml.) and the combined extracts dried ($MgSO_4$) and the solvent removed to give a residual oil which was distilled at 0.2 mm to give 1,2,3,4,5,7,8,9,10,11-decahydrodicyclohepta[b,e]pyridine (30 g.) b.p. 120° C. which was dissolved in ether (100 ml.) and added to isopropylmagnesium bromide [prepared from isopropylbromide (18.3 g.) and magnesium (4.8 g.) in ether (30 ml.)]. The mixture was heated in an oil bath at 140° C and the ether distilled out and replaced by toluene (50 ml.). The reaction mixture was heated for a further 4 hours, cooled and diluted with ether (200 ml.) and the resulting solution of 1,2,3,4,5,7,8,9,10,11-decahydrodicyclohepta[b,e]-pyridine-5-magnesium bromide added to ether (500 ml.) whilst a rapid stream of $CO_2$ gas was passed through the mixture. The resultant solid (the magnesium bromide salt of 1,2,3,4,5,7,8,9,10,11-decahydrodicyclohepta[b,e]pyridine 5-carboxylic acid) was filtered off and added to a solution of methanol saturated with HCl (700 ml.) at 0° C. and allowed to stand at room temperature overnight. The solvent was removed and the residue dissolved in water (150 ml.) and the solution washed with ether (3 × 100 ml.) The pH was adjusted to 10.0 with sodium carbonate and extracted with ether (3 × 100 ml.) and the combined extracts dried ($MgSO_4$) and the solvent removed. The residual oil, methyl 1,2,3,4,5,7,8,9,10,11-decahydrodicyclohepta[b,e]pyridine-5-carboxylate (26 g.) was dissolved in methanol saturated with ammonia (500 ml.) and the solution heated in a sealed reactor at 100° C. for 18 hours. The solvent was removed and the residue chromatographed on silica gel. Elution with 5% methanol-chloroform gave 1,2,3,4,5,7,8,9,10,11-decahydro-dicyclohepta[b,e]pyridine-5-carboxyamide as colourless needles (1.5 g.) m.p. 179° C. (Found: C, 74.5; H, 8.7; N, 10.7. $C_{16}H_{22}N_2O$ requires: C, 74.4; H, 8.6; N, 10.9%).

EXAMPLE 4

Methyl-1,2,3,5,6,7-Hexahydro-dicyclopenta[b,e]pyridine-3-carboxylate

A mixture of 2-dimethylaminomethyl)cyclopentanone (87 g.) and cyclopentanone (210 g.) was heated at reflux for 12 hours. The excess cyclopentanone was removed by distillation and the residue was dissolved in ethanol (300 ml.) and treated with hydroxylamine hydrochloride (100 g.) and the mixture heated at reflux for 1½ hours. The cooled reaction mixture was dissolved in water (1 liter), washed with ether (3 × 200 ml.) and the aqueous phase adjusted to pH 10.0 with sodium carbonate and extracted with ether (3 × 200 ml.). The combined extracts were dried ($MgSO_4$) and the solvent removed to give a residual oil which was distilled at 0.2 mm to give 1,2,3,5,6,7-hexahydrodicyclopenta[b,e]pyridine as a colourless oil (50 g.) b.p. 100° C. The oil was treated with isopropyl magnesium bromide following the procedure of Example 3 to obtain 1,2,3,5,6,7-hexahydro-dicyclopenta[b,e]pyridine-3-magnesium bromide which was treated with $CO_2$ gas following the procedure of Example 3 to obtain the magnesium bromide salt of 1,2,3,5,6,7-hexahydro-dicyclopenta[b,e]pyridine-3-carboxylic acid which was converted to the title compound in the manner described in Example 3. The title compound was converted to the amide by treatment with methanol saturated with ammonia in the manner described in Example 3. 1,2,3,5,6,7-hexahydro-dicyclopenta[b,e]pyridine-3-carboxamide (2 g.) was isolated as colourless needles from methanol, m.p. 188° C. (Found: C, 71.1; H, 7.2; N, 14.3. $C_{12}H_{14}N_2O$ requires: C, 71.4; H, 7.0; N, 13.9%).

EXAMPLE 5

Methyl-3-methylcyclopenteno[b]pyridine-7-carboxylate and
3-methyl-cyclopenteno[b]pyridine-7-carboxamide 3-methyl-cyclopenteno[b]pyridine (13.1 g.) in ether (130 ml.) was added to isopropylmagnesium bromide [prepared from magnesium 6.3 g and isopropylbromide 24.2 g in a total of 40 ml ether]. The mixture was heated at 120° C for 5 hours adding toluene when necessary as the ether distilled off to maintain the contents liquid. The mixture was cooled and ether (200 ml) added. The ethereal solution of 3-methyl-cyclopenteno[b]pyridine-7-magnesium bromide was added to stirred ice-cooled ether (500 ml) whilst a stream of dry $CO_2$ gas was bubbled through until the red colour had discharged. The resulting solid (the magnesium bromide salt of 3-methyl-cyclopenteno[b]pyridine-7-carboxylic acid) was dried and added to methanol (500 ml) saturated with HCl. The solution was stirred overnight then evaporated to dryness. The residue was dissolved in water and extracted with ether. The aqueous phase was basified with sodium carbonate, any solid was filtered off and the aqueous solution was extracted with ether (3 times). The ether extract was dried and evaporated to dryness leaving an oil which was purified by distillation at 0.2 mm. to give methyl-3-methylcyclopenteno[b]pyridine-7-carboxylate (2.4 g., b.p. 103°–110° C). The ester was dissolved in methanol saturated with ammonia in a bomb and kept overnight at 80° C. The solution was cooled and evaporated to dryness. The product was purified by chromatography and recrystallised from ethyl acetate to give the amide title compound m.p. 150° C. [Analysis Found: 68.0; H, 7.1 N, 15.8, $C_{10}H_{12}N_2O$ requires C, 68.2, H, 6.9 N, 15.9%]

EXAMPLE 6

Following the general procedure of Example 1 but employing the alternative starting materials indicated the specified magnesium halide products can be prepared.

| | End Products | |
|---|---|---|
| Starting Material | Magnesium Halide derivative | Magnesium Halide Salt |
| 2-Phenyl-5,6,7,8-tetrahydroquinoline | 2-phenyl-5,6,7,8-tetrahydroquinoline-8-magnesium bromide | 2-phenyl-5,6-7,8-tetrahydroquinoline 8-carboxylic acid, magnesium bromide salt. |

| Starting Material | End Products Magnesium Halide derivative | Magnesium Halide Salt |
|---|---|---|
| 5,6,7,8-tetrahydro-quinoline | 5,6,7,8-tetrahydro-quinoline-8-magnesium bromide | 5,6,7,8-tetra-hydroquinoline-8-carboxylic acid, magnesium bromide salt. |
| 2-t-butyl-5,6,7,8-tetrahydroquinoline | 2-t-butyl-tetrahydro-quinoline-8-magnesium bromide | 2-t-butyl-tetra-hydroquinoline-8-carboxylic acid, magnesium bromide salt. |
| sym-octahydroacridine | octahydroacridine-4-magnesium bromide | octahydroacridine-4-carboxylic acid, magnesium bromide salt. |
| 3-methylcyclohepteno[b]pyridine | 3-methylcyclo-hepteno[b]pyridine 9-magnesium bromide | 3-methylcyclohepteno[b]pyridine-9-carboxylic acid, magnesium bromide salt. |
| 3,7,7-trimethyl-5,6,7,8-tetrahydro-quinoline | 3-7,7-trimethyl-5,6,7,8-tetrahydro-quinoline-8-magnes-ium bromide | 3,7,7-trimethyl-5,6,7,8-tetrahydro-quinoline-8-carboxylic acid-magnesium bromide salt. |
| 4-methyl-5,6,7,8-tetrahydroquinoline | 4-methyl-5,6,7,8-tetrahydro-quinoline-8-magnesium bromide | 4-methyl-5,6,7,8-tetrahydroquinoline-8-carboxylic acid-magnesium bromide salt. |
| 3,4-dimethyl-5,6,7,8-tetrahydroquinoline | 3,4-dimethyl-5,6,7,8-tetrahydro-quinoline-8-magnesium bromide | 3,4-dimethyl-5,6,7,8-tetrahydro-quinoline-8-carboxylic acid magnesium bromide salt. |

EXAMPLE 7

Following the general procedure of Examples 1, 3, 4 or 5 but replacing isopropyl bromide by an equivalent amount of isopropyl chloride the following compounds can be prepared from the indicated starting materials.

| | End Products | |
|---|---|---|
| 3-methyl-5,6,7,8-tetra-hydroquinoline | 3-methyl,5,6,7,8-tetrahydro-quinoline-8-magnes-ium chloride | 3-methyl-5,6,7,8-tetrahydroquinoline 8-carboxylic acid magnesium chloride salt. |
| 1,2,3,4,5,7,8,9,10 11-decahydro-dicyclohepta[b,e]pyridine | 1,2,3,4,5,7,8,9,10,11-decahydro-dicyclohepta[b,e]pyridine-5-magnesium chloride. | 1,2,3,4,5,7,8,9,10.11-decahydro-dicyclohepta[b,e]pyridine-5-carboxylic acid magnesium chloride salt. |
| 1,2,3,5,6,7-hexahydro-dicyclopenta[b,e]pyridine | 1,2,3,5,6,7-hexahydro-dicyclopenta[b,e]pyridine 3-magnesium chloride | 1,2,3,5,6,7-hexyhydro di-cyclopenta[b,e]pyridine 3-carboxylic acid magnesium chloride salt. |
| 3-methyl-cyclopent-eno[b]-pyridine | 3-methyl-cyclopent-eno[b]-pyridine-7b-magnesium chloride | 3-methyl-cyclo-penteno[b]-pyridine-7-carboxylic acid magnesium chloride salt. |

I claim:
1. A compound of formula (II)

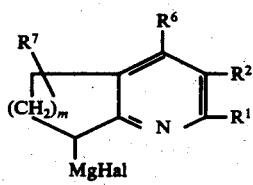

wherein
$R^1$, $R^2$ and $R^6$ are independently hydrogen, alkyl of 1 to 6 carbon atoms, phenylalkyl of 7 to 12 carbon atoms, phenyl, alkylphenyl of 7 to 12 carbon atoms, alkoxyphenyl of 7 to 12 carbon atoms, or halophenyl, or $R^1$ and $R^2$ taken together, are trimethylene, tetramethylene or pentamethylene or an $R^7$ substituted derivative thereof;
$R^7$ is hydrogen, alkyl of 1 to 6 carbon atoms, gem-dimethyl, phenylalkyl of 7 to 12 carbon atoms, phenyl, alkylphenyl of 7 to 12 carbon atoms, alkoxyphenyl of 7 to 12 carbon atoms, or halophenyl;
$m$ is 1 or 3; and
Hal represents chlorine, bromine or iodine, with the proviso that when $R^1$ and $R^2$ or $R^2$ and $R^6$ are both alkyl, they are selected from normal and secondary alkyl groups.

2. A compound of formula (II)

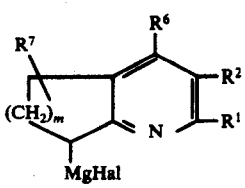

wherein
R[1] is hydrogen, alkyl of 1 to 6 carbon atoms or phenyl,
R[2] is hydrogen or alkyl of 1 to 6 carbon atoms,
R[6] is hydrogen or alkyl of 1 to 6 carbon atoms, or
R[1] and R[2] taken together are trimethylene, tetramethylene, or pentamethylene or a R[7] substituent derivative thereof,
R[7] is hydrogen, alkyl of 1 to 6 carbon atoms or gem-dimethyl (in the 5, 6 or 7 positions),
m is 1 or 3, and
Hal is chlorine, bromine or iodine, with the proviso that when R[1] and R[2] or R[2] and R[6] are both alkyl, they are selected from normal and secondary alkyl groups.

3. A compound as claimed in claim 1, wherein m is 3 and R[1] and R[2], taken together are, pentamethylene.

4. The compound as claimed in claim 2, which is 1,2,3,4,5,7,8,9,10,11-decahydrodicyclohepta[b,e]-pyridine-5-magnesium bromide.

5. A compound as claimed in claim 1, wherein m is 1 and R[1] and R[2], taken together are trimethylene.

6. The compound claimed in claim 5 which is 1,2,3,5,6,7-hexahydro-dicyclopenta[b,e]pyridine-3-magnesium bromide.

7. A compound as claimed in claim 1, wherein m is 1, R[2] is methyl and R[1], R[6] and R[7] are hydrogen.

8. The compound as claimed in claim 7 which is 3-methylcyclopenteno[b]pyridine-7-magnesium bromide.

9. A compound as claimed in claim 1 wherein m is 3, R[2] is methyl and R[1], R[6] and R[7] are hydrogen.

10. The compound as claimed in claim 9 which is 3-methylcyclohepteno[b]pyridine-9-magnesium bromide.

* * * * *